US00PP31029P2

(12) United States Plant Patent
Ren et al.

(10) Patent No.: US PP31,029 P2
(45) Date of Patent: Nov. 5, 2019

(54) ***ECHINACEA* PLANT NAMED 'BALEVOESTA'**

(50) Latin Name: ***Echinacea* x *hybrida***
Varietal Denomination: Balevoesta

(71) Applicant: Ball Horticultural Company, West Chicago, IL (US)

(72) Inventors: Jianping Ren, Geneva, IL (US); Richard H. Wells, McMinnville, OR (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/350,242

(22) Filed: Oct. 17, 2018

(51) Int. Cl.
*A01H 5/02* (2018.01)
*A01H 6/14* (2018.01)

(52) U.S. Cl.
USPC ..... Plt./428

(58) Field of Classification Search
USPC ..... Plt./428
CPC . A01H 5/025; A01H 5/02; A01H 5/00; A01H 6/14; A01H 6/1448
See application file for complete search history.

*Primary Examiner* — June Hwu
(74) *Attorney, Agent, or Firm* — Audrey Charles

(57) ABSTRACT

A new and distinct cultivar of *Echinacea* plant named 'Balevoesta', characterized by its single-type, reddish-orange to red colored inflorescences that first open a reddish yellow-orange color and fade to a greyed purplish-red color with age, medium green-colored foliage, and moderately vigorous, compact-upright growth habit, is disclosed.

1 Drawing Sheet

Latin name of genus and species of plant claimed: *Echinacea* x *hybrida.*

Variety denomination: 'Balevoesta'.

BACKGROUND OF THE INVENTION

The present invention relates to a new and distinct cultivar of *Echinacea* plant botanically known as *Echinacea* x *hybrida* and hereinafter referred to by the cultivar name 'Balevoesta'.

The new *Echinacea* cultivar is a novel seedling selection from 'Cheyenne Spirit', protected under a breeding method claim in U.S. Pat. No. 7,982,110, a segregating mix characterized by single-type inflorescences having a range of flower colors that include shades of red, orange, purple, scarlet, cream, yellow and white, medium green-colored foliage, and moderately vigorous, upright growth habit. The new cultivar was discovered as a whole plant and selected during July 2014 in a controlled environment in Dayton, Oreg.

Asexual reproduction of the new cultivar by in vitro shoot propagation since July 2015 in Dayton, Oreg. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balevoesta' as a new and distinct cultivar of *Echinacea* plant:

1. Single-type, reddish-orange to red colored inflorescences that first open a reddish yellow-orange color and fade to a greyed purplish-red color with age;

2. Medium green-colored foliage; and
3. Moderately vigorous, compact-upright growth habit.

Plants of the new cultivar differ from plants of the parent primarily in having a novel combination of characteristics including ray floret color, ray floret size, and plant habit.

Of the many commercially available *Echinacea* cultivars, the most similar in comparison to the new cultivar is SOMBRERO Baja Burgundy 'Balsombabur', U.S. Plant Pat. No. 28,162. However, in side by side comparisons, plants of the new cultivar differ from plants of 'Balsombabur' in at least the following characteristics:

1. Plants of the new cultivar have more main stems per plant than plants of 'Balsombabur';
2. Plants of the new cultivar have a ray floret color that opens a reddish yellow-orange color that is different from the first open red color of ray florets of plants of 'Balsombabur'; and
3. Plants of the new cultivar have more inflorescences per plant than plants of 'Balsombabur'.

BRIEF DESCRIPTION OF THE PHOTOGRAPHS

The accompanying photographs show, as nearly true as it is reasonably possible to make the same in color illustrations of this type, typical inflorescence and foliage characteristics of the new cultivar. Colors in the photographs differ slightly from the color values cited in the detailed description, which accurately describes the colors of 'Balevoesta'. The plants were approximately five months old and grown in Elburn, Ill. in one-gallon containers for approximately three months.

DETAILED BOTANICAL DESCRIPTION

Figure 1:
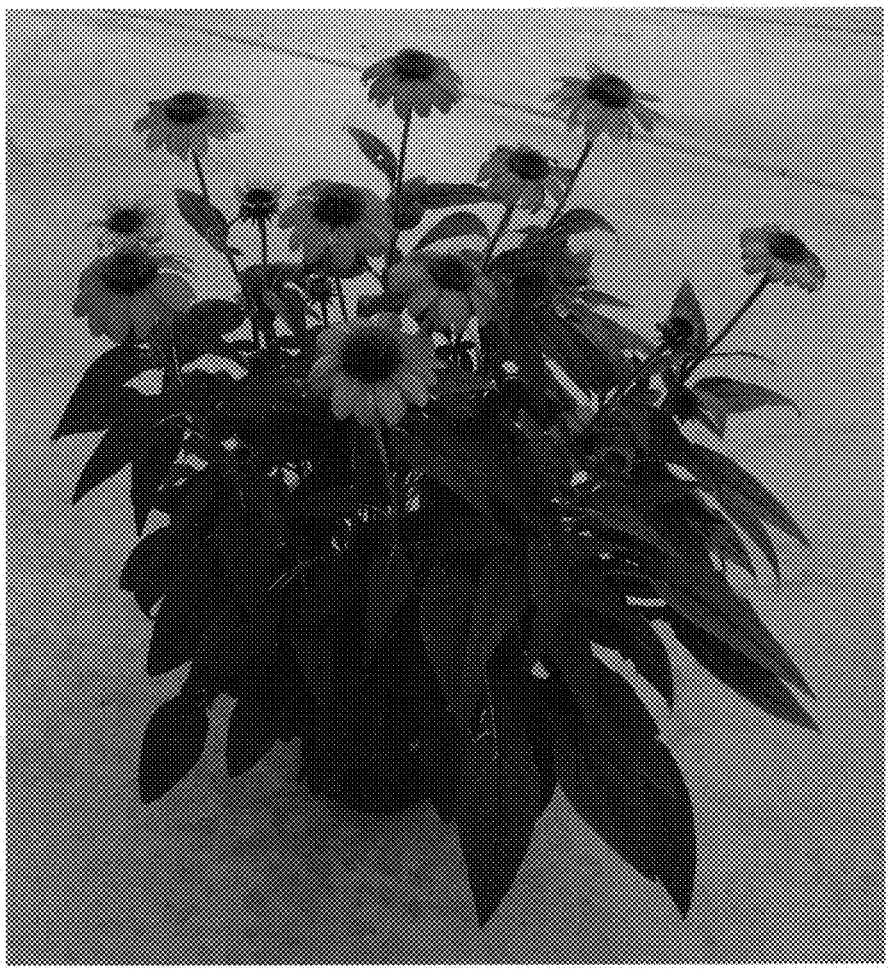
FIG. 1 illustrates a side view of the overall growth and flowering habit of 'Balevoesta'.
Figure 2:
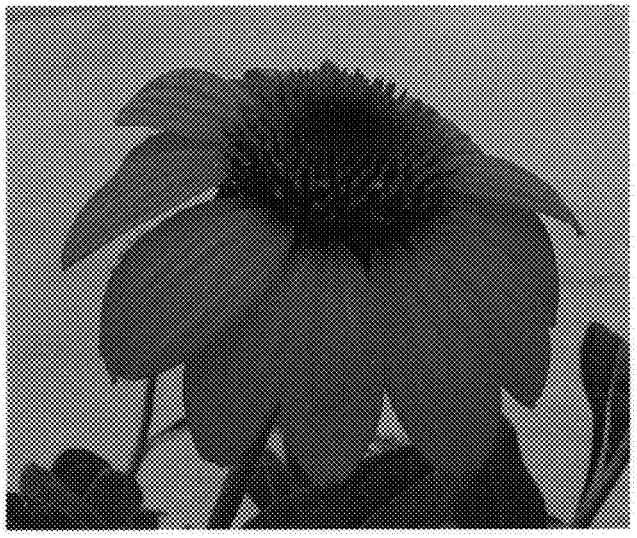
FIG. 2 illustrates a close-up view of an individual inflorescence of 'Balevoesta'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately five-month old plants produced from in vitro plantlets and grown utilizing a soilless growth medium under conditions comparable to those used in commercial practice. The plants were grown in Elburn, Ill. in one-gallon containers in a glass-covered greenhouse for approximately three months. Greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided. Measurements and numerical values represent averages of typical plants.

Botanical classification: *Echinacea* x *hybrida* 'Balevoesta'.

Parentage:

*Parent*.—'Cheyenne Spirit', protected under breeding method claim of U.S. Pat. No. 7,982,110.

Propagation:

*Type*.—In vitro propagation is preferred, divisions are possible.

*Time to initiate roots in vitro*.—Approximately 30 days at 18° C.

*Time to produce a rooted plantlet in summer*.—Approximately 30 days at 18° C.

*Root description*.—Fine, fibrous; grey to light brown in color.

*Rooting habit*.—Moderate density, moderate branching.

Plant description:

*Commercial crop time*.—Approximately 10 to 12 weeks from a rooted tissue culture plantlet to finish in a 15 cm container.

*Growth habit and general appearance*.—Herbaceous perennial, moderately vigorous, compact-upright.

*Hardiness*.—USDA Zone 5a (−20° F. to −15° F./−28.9 ° C. to −26° C.).

*Size*.—Height from soil level to top of plant plane: Approximately 53.0 cm. Width: Approximately 48.0 cm.

*Branching habit*.—No lateral branching, flowering stems grow from base. Quantity of main stems per plant: Approximately 16.

*Stems*.—Strength: Very strong. Aspect: Nearly erect. Shape: Rounded. Length to base of inflorescence: Approximately 51.0 cm. Diameter: Approximately 4.0 mm to 6.0 mm. Length of central internode: Approximately 6.5 cm. Texture: Densely pubescent with short strigose hairs. Color of young stems: 146C. Color of mature stems: 146B.

Foliage description:

*General description*.—Form: Simple. Arrangement: Alternate.

*Leaves*.—Aspect: Perpendicular to stem, subtending with age. Shape: Narrowly ovate to lanceolate. Margin: Entire to shallowly serrate, very slightly undulate. Apex: Acute. Base: Attenuate. Venation pattern: Pinnate. Length of mature leaf: Approximately 10.0 cm to 14.0 cm. Width of mature leaf: Approximately 4.0 cm to 6.0 cm. Texture of upper surface: Dull, moderately pubescent with short strigose hairs. Texture of lower surface: Moderately pubescent with short strigose hairs. Color of upper surface of young and mature foliage: Closest to NN137A with venation of 147C. Color of lower surface of young and mature foliage: Closest to 137A with venation of 147D.

*Petiole*.—Shape: V-shaped. Length: Approximately 5.0 cm to 19.0 cm. Diameter: Approximately 3.0 mm. Texture of upper surface: Glabrous. Texture of lower surface: Sparsely covered with very short strigose hairs. Color of upper and lower surfaces: 147D.

Flowering description:

*Flowering habit*.—'Balevoesta' is freely flowering under outdoor growing conditions blooming from late spring through late summer and with limited flowering under short winter days in a greenhouse environment.

*Lastingness of individual inflorescence on the plant*.—Approximately 3 weeks.

Inflorescence description:

*General description*.—Type: Solitary, composite. Persistent. Shape: Conical. Aspect: Facing upward. Arrangement: Terminal, held upright on strong peduncles. Fragrance: Faintly sweet. Quantity per plant: Approximately 11. Height: Approximately 3.5 cm. Diameter: Approximately 7.0 cm.

*Peduncle*.—Strength: Moderately strong. Aspect: Erect to approximately 45° from vertical. Length: Approximately 13.0 cm. Diameter: Approximately 3.0 mm to 4.0 mm. Texture: Densely pubescent with short strigose hairs. Color: 146B.

*Bud*.—Quantity per plant: Approximately 7. Shape: Flattened globular with immature ray florets nearly erect. Length: Approximately 1.7 cm. Diameter: Approximately 1.7 cm. Color: Outer ray florets of 145A; bud center of 143A.

*Ray florets*.—Quantity per inflorescence: Approximately 17. Arrangement: In a single whorl, slightly imbricate. Aspect: Perpendicular to disc, subtending slightly with age. Shape: Elliptic to narrowly obovate. Appearance: Dull. Margin: Entire. Apex: Emarginate to notched. Base: Attenuate. Length: Approximately 3.7 cm. Width: Approximately 1.4 cm. Texture of upper surface: Glabrous, ribbed longitudinally. Texture of lower surface: Sparsely pubescent, ribbed longitudinally. Color of upper surface when first open: N25D with N34B. Color of lower surface when first open: 155D with an overlay of 186C. Color of upper surface when fully open: 44A with 44B, with age darkening to 46A with 46B and 185C at senescence. Color of lower surface when fully open: 155D with an overlay of 186C to 186D.

*Disc florets*.—Disc diameter: Approximately 3.0 cm. Quantity per inflorescence: Approximately 225. Arrangement: Spirally arranged in center of inflorescence. Shape: Tubular. Margin of free portion: Entire. Apex: Five acute tips. Base: Fused into a tube. Length: Approximately 1.1 cm. Diameter: Approximately 2.0 mm. Texture: Glabrous. Color of upper or inner surface when first and fully open:

146C with tips of 187A. Color of lower or outer surface when first and fully open: 146C with tips of 187A and base of 155D.

*Receptacle*.—Shape: Conical. Height: Approximately 1.5 cm. Diameter: Approximately 1.2 cm. Color: 155D.

*Phyllaries*.—Quantity per inflorescence Approximately 50. Arrangement: In whorls. Appearance: Dull, stiff. Shape: Narrowly ovate to lanceolate, strongly curved towards the peduncle. Margin: Entire, ciliate. Apex: Acute. Base: Truncate. Length: Approximately 1.1 cm. Width: Approximately 2.0 mm to 3.0 mm. Texture of upper or inner surface: Glabrous. Texture of lower or outer surface: Sparsely pubescent with short strigose hairs. Color of upper surface: 137A. Color of lower surface: 137B.

*Receptacle spines*.—Number of spines per disc: Approximately 225. Shape: Acicular. Length: Approximately 1.3 cm. Width at widest point: Approximately 2.0 mm. Apex: Acute. Base: Truncate. Texture: Glabrous. Color: Apex of 167B with a heavy overlay and tip of 187A, mid-section of 144A, and base of 155D.

*Reproductive organs*.—Androecium: Present on disc florets only. Stamen quantity: 5 per floret. Anther shape: Oblong, basifixed. Anther length: Approximately 3.0 mm. Anther color: Closest to 203B. Filament length: Approximately 2.0 mm. Filament color: 145D. Pollen amount: Moderate. Pollen color: 17B. Gynoecium: Present on disc florets only. Pistil quantity: 1 per floret. Pistil length: Approximately 1.1 cm. Stigma shape: Bifid, curled. Stigma length: Approximately 2.0 mm. Stigma color: 187A. Style length: Approximately 7.0 mm. Style color: 145D. Ovary length: Approximately 3.0 mm. Ovary color: 155D.

Seed and fruit production: Neither seed nor fruit production has been observed.

Disease and pest resistance: No particular resistance or susceptibility to other diseases or insects noted to date.

What is claimed is:

1. A new and distinct cultivar of *Echinacea* plant named 'Balevoesta', substantially as herein illustrated and described.

* * * * *